United States Patent
Zhao et al.

(10) Patent No.: US 6,524,247 B2
(45) Date of Patent: Feb. 25, 2003

(54) METHOD AND SYSTEM FOR ULTRASOUND IMAGING OF A BIOPSY NEEDLE

(75) Inventors: Danhua Zhao, Milpitas, CA (US); Tommy Earl Cupples, Columbia, SC (US); Zengpin Yu, Palo Alto, CA (US)

(73) Assignee: U-Systems, Inc., San Jose, CA (US)

( * ) Notice: Subject to any disclaimer, the term of this patent is extended or adjusted under 35 U.S.C. 154(b) by 0 days.

(21) Appl. No.: 09/858,221

(22) Filed: May 15, 2001

(65) Prior Publication Data

US 2002/0173719 A1 Nov. 21, 2002

(51) Int. Cl.$^7$ ................................................ A61B 8/00
(52) U.S. Cl. ........................ 600/437; 600/443; 600/461
(58) Field of Search ................................ 600/437, 443, 600/447, 461, 463, 467, 471; 128/916

(56) References Cited

U.S. PATENT DOCUMENTS

| | | | |
|---|---|---|---|
| 5,704,361 A | * 1/1998 | Seward et al. | 600/466 |
| 5,911,221 A | * 6/1999 | Teo | 600/447 |
| 6,048,312 A | 4/2000 | Ishrak et al. | |
| 6,063,030 A | 5/2000 | Vara et al. | |
| 6,117,081 A | 9/2000 | Jago et al. | |
| 6,126,598 A | 10/2000 | Entrekin et al. | |
| 6,126,599 A | 10/2000 | Jago et al. | |
| 6,135,956 A | 10/2000 | Schmiesing et al. | |
| 6,146,329 A | * 11/2000 | Hayakawa | 600/461 |
| 6,210,328 B1 | 4/2001 | Robinson et al. | |
| 6,336,899 B1 | * 1/2002 | Yamazaki | 600/443 |

OTHER PUBLICATIONS

Gonzalez, *Digital Image Processing*, Addison–Wesley Publishing Co. (1992), cover page and table of contents.

(List continued on next page.)

*Primary Examiner*—Francis J. Jaworski
(74) *Attorney, Agent, or Firm*—Cooper & Dunham LLP (57) ABSTRACT

A method, system, computer program product, and user interface for real-time ultrasonic visualization enhancement of a biopsy needle are disclosed in which a wide range of needle positions with respect to the ultrasound probe axis and with respect to the imaged plane are accommodated. Ordinary frames are compounded with special purpose frames, the special purpose frames having transmit and receive parameters adapted to highlight reception of echoes from the biopsy needle. Preferably, an elevation beam width associated with the special purpose ultrasound frames is wider than an elevation beam width associated with the ordinary ultrasound frames. Preferably, the beams of the special purpose ultrasound frames are steered such that they are incident upon the biopsy needle at an increased angle as compared to the angle of incidence for ordinary ultrasound frames. A method for automatically and adaptively determining the depth and orientation of a biopsy needle is also described, whereby beam steering parameters, focus parameters, etc. may be automatically and adaptively computed. The user may optionally provide selected beam steering parameters to the ultrasound imaging system using a simple, intuitive user interface.

29 Claims, 8 Drawing Sheets

OTHER PUBLICATIONS

X.Y. Cheng, et al. "Automated Detection of Breast Tumors in Ultrasonic Images Using Fuzzy Reasoning," Proceedings of the International Conference on Image Processing, vol. III, pp. 420–423, IEEE Computer Society (Oct. 26–29, 1997).

Cheng, et al., *A Study on Automated Extraction of Breast Tumors Using Three Dimensional Ultrasonic Echography*, Ph.D Thesis, Keio University, Japan (1997).

U.S. patent application Ser. No. 09/224,635 filed Dec. 31, 1998.

U.S. patent application Ser. No. 09/449,095 filed Nov. 24, 1999.

U.S. patent application Ser. No. 09/571,197 filed May 16, 2000.

U.S. patent application Ser. No. 09/721,889 filed Nov. 24, 2000.

* cited by examiner

METHOD AND SYSTEM FOR ULTRASOUND IMAGING OF A BIOPSY NEEDLE

FIELD

This patent specification relates to medical ultrasound imaging systems. In particular, it relates to a method and system for enhanced ultrasonic viewing of a specular instrument such as a biopsy needle inserted into the body during a medical procedure.

BACKGROUND

Ultrasound imaging systems are being increasingly used in medical diagnosis, surgery, and treatment because they are non-invasive, easy to use, capable of real-time operation, and do not subject patients to the dangers of electromagnetic radiation. Instead of electromagnetic radiation, an ultrasound imaging system transmits sound waves of very high frequency (e.g., 1 MHz to 15 MHz) into the patient and processes echoes scattered from structures in the patient's body to derive and display information relating to these structures.

Among the many practical applications of ultrasound imaging systems is their use during invasive or partially invasive medical procedures for allowing the medical professional to better visualize and control the procedure. For example, a breast biopsy is a medical procedure in which a specialized biopsy needle is inserted into the breast to extract tissue samples of a suspicious lesion or tumor. The biopsy needle must be accurately guided so that its tip enters the lesion. Using an ultrasound imaging system, the physician or other medical professional (hereinafter "user") can guide the biopsy needle by viewing real-time ultrasound images of the biopsy needle with respect to the target lesion.

A problem, however, arises in practical clinical applications as a result of the thin, specular nature of most biopsy needles. Because they are elongated and narrow, biopsy needles often elude the plane of the ultrasound slice being imaged. When they do intersect this plane, it is often for only brief intervals of time or space.

Another problem arises from the smooth, metallic nature of most biopsy needles. These needles are specular reflectors that, unlike the tissues in the patient's body, do not reflect incident ultrasound pulses in a diffuse manner. This makes the biopsy needle difficult to perceive in the ultrasound output image unless the incident ultrasound pulses approach the biopsy needle at angles close to ninety degrees. Only for those angles close to ninety degrees will the incident pulses be reflected back to the probe transducer array and properly detected. This problem is alleviated somewhat for abdominal procedures (e.g. for heart, liver, and prenatal procedures) that predominantly use curvilinear imaging formats. For curvilinear imaging formats, the scan lines spread out over a substantial ranges of angles, some of which are perpendicular, or close to perpendicular, to the biopsy needle. In contrast, the predominant imaging format for breast biopsy procedures is the linear format, in which the scan lines are generally parallel to each other, thereby making biopsy needle visualization more difficult for many angles. Nevertheless, it is to be appreciated that the preferred embodiments described infra may be used to enhance needle visualization for any type of imaging format, including linear formats, steered linear formats, curvilinear formats, sector formats, vector formats, and other formats.

U.S. Pat. No. 6,048,312 (hereinafter "the '312 patent"), which is incorporated by reference herein, discusses a method for three-dimensional ultrasound imaging of a needle-like instrument, such as a biopsy needle, in which the transmitted ultrasound beams are steered to increase the angle at which they impinge upon the biopsy needle. This increases the system's sensitivity to the needle because the reflections from the needle are directed closer to the transducer array. The steered image frames, i.e., the image frames formed from the steered ultrasound beams, may be superimposed with non-steered image frames to form a composite image, and the needle may be highlighted using an intensity-mapping procedure. When the position of the biopsy needle is undetermined, a non-steered first image frame may be combined with a second image frame acquired by steering the beam at a constant first steering angle and with a third image frame acquired by steering the beam at a constant second steering angle, to increase visibility of the biopsy needle.

However, the '312 patent leaves several problems associated with biopsy needle imaging unresolved. For example, while the beams are steered by a transmitter and receiver that "are operated under control of a host computer or master controller [ ] responsive to commands by a human operator," (col. 5, lines 63–65), the nature of the system's determination of the biopsy needle position is not clear. As another example, the acquired 2-D ultrasound slices have reduced visibility of the biopsy needle when it is positioned out-of-plane with respect to the ultrasound slice. As described supra, this problem is caused by the elongated, narrow shape of the biopsy needed. This problem can be at least partially remedied by a method disclosed in the '312 patent, a "cut plane rotate" method, in which the user graphically manipulates a slice within a 3-D volume construction of the target region until the biopsy needle is coplanar with the slice, wherein data from the 3D volume corresponding to the slice is then displayed (col. 11, lines 18–44). However, this process is highly computationally intensive, and may therefore be difficult to achieve in a real-time system in a cost-effective manner. Moreover, this procedure demands a substantial amount of user attention and manipulation of the ultrasound user interface. Often, the user is already highly occupied with the biopsy procedure being performed, and does not want to devote an undue amount of time and attention to a system that is supposed to be making things easier.

Accordingly, it would be desirable to provide an ultrasound system with real-time biopsy needle visualization enhancement for a wide range of needle positions with respect to the probe.

It would be further desirable to provide such an ultrasound system in which biopsy needle visualization may be enhanced when the needle position is not predetermined or provided to the system by the user.

It would be further desirable to provide such an ultrasound system having an optional mode in which estimates of the position of the biopsy needle may be easily provided by the user, the ultrasound system having an intuitive, easy-to-use user interface that does not require excessive user manipulation.

It would be even further desirable to provide such an ultrasound system in which biopsy needle visualization may be enhanced even when the biopsy needle may wander or deviate from the plane of the ultrasound slice being imaged.

It would be still further desirable to provide such an ultrasound system that provides such biopsy needle visualization enhancement without requiring the computational intensity associated with 3-D volume construction.

SUMMARY

A method and system for real-time visualization enhancement of a biopsy needle are provided, wherein a wide range of needle positions with respect to the probe axis and with respect to the imaged plane are accommodated. Ordinary ultrasound frames are compounded with special purpose ultrasound frames and then output to a real-time display, the special purpose ultrasound frames having transmit and receive parameters adapted to highlight reception of ultrasound echoes from the biopsy needle. In one preferred embodiment, an elevation beam width associated with the special purpose ultrasound frames is wider than an elevation beam width associated with the ordinary ultrasound frames. This reduces sensitivity to the position of the biopsy needle with respect to the imaged plane, and increases reception of biopsy needle echoes in cases where the biopsy needle deviates from the imaged plane. Methods for increasing the elevation beam width of the special purpose frames include lowering the operating frequency and managing the elevation aperture.

Preferably, the beams of the special purpose ultrasound frames are steered such that they are incident upon the biopsy needle at an increased angle as compared to the angle of incidence for ordinary ultrasound frames. For cases in which both the biopsy needle depth and the biopsy needle angle are known, each scan line of the special purpose ultrasound frames has an independently-assigned lateral focus depth equal to a distance between the transducer array and the biopsy needle along that scan line. The biopsy needle image is improved because each point on the needle is in focus with respect to the lateral dimension of the ultrasound image. Edge enhancement, noise/clutter suppression, thresholding, segmentation, or other image processing algorithms may be performed on the special purpose frames prior to compounding. Lesion-enhancement algorithms may also be applied to the special purpose frames and/or to the ordinary frames, wherein both the target lesion and the biopsy needle appear highlighted on the user display.

Processing time for the special purpose frames may be reduced, and therefore overall frame rate increased, by reducing the number of scan lines in the special purpose frame. Because the biopsy needle shape is predictably straight, it has been found that needle image quality does not appreciably deteriorate even when the number of scan lines is decreased by 50 percent or more from the number of scan lines in the ordinary image. Furthermore, several of the image processing algorithms performed on the special purpose frames, including edge enhancement and noise/clutter suppression, may be one-dimensional in nature and separately applied to the scan lines for further reducing processing time.

Values for the needle depth and orientation may be fixed to a known value (e.g., where a fixed mechanical needle guide is used), may be provided by a position sensing system, may be provided by the user, or may be automatically and dynamically determined in accordance with a preferred embodiment described herein. According to a preferred embodiment, a fast method for automatically determining the depth and orientation of a biopsy needle is provided, wherein an exploratory beam is swept across the target region, at periodic or non-periodic intervals, across a wide range of angles. Echoes from the exploratory beam are then processed in a substantially one-dimensional algorithm, or optionally in a two-dimensional algorithm, to determine the depth and orientation of the biopsy needle. The ultrasound beams for the special purpose frames may then be steered to the computed orientation and laterally focused according to the computed depth. The ultrasound system thereby automatically adapts to the position of the biopsy needle for providing enhanced visualization thereof.

According to another preferred embodiment, a simplified method and user interface therefor are provided for enhancing biopsy needle visualization, in which respective special purpose frames are steered at a plurality of predetermined angles, wherein the special purpose frames are compounded with ordinary frames and output to a display. In one preferred embodiment, only a few angles (e.g., +30 degrees and −30 degrees) are taken for the special purpose frames. In another preferred embodiment, a plurality of angles are used, the number of angles being not less than a quotient of a maximum field angle divided by a critical separation angle. It has been found that this critical separation angle is typically between about 10 to 16 degrees. In one embodiment, a single toggle button is provided to the user that activates a needle enhancement mode and selects the number of steering angles to be used. In another preferred embodiment, a plurality of toggled selection buttons is presented to the user in a spatial pattern that emulates predetermined ranges of needle angles, whereby the user may intuitively select the number and direction of steering angles to be used for the special purpose frames.

DETAILED DESCRIPTION

Figure 1:
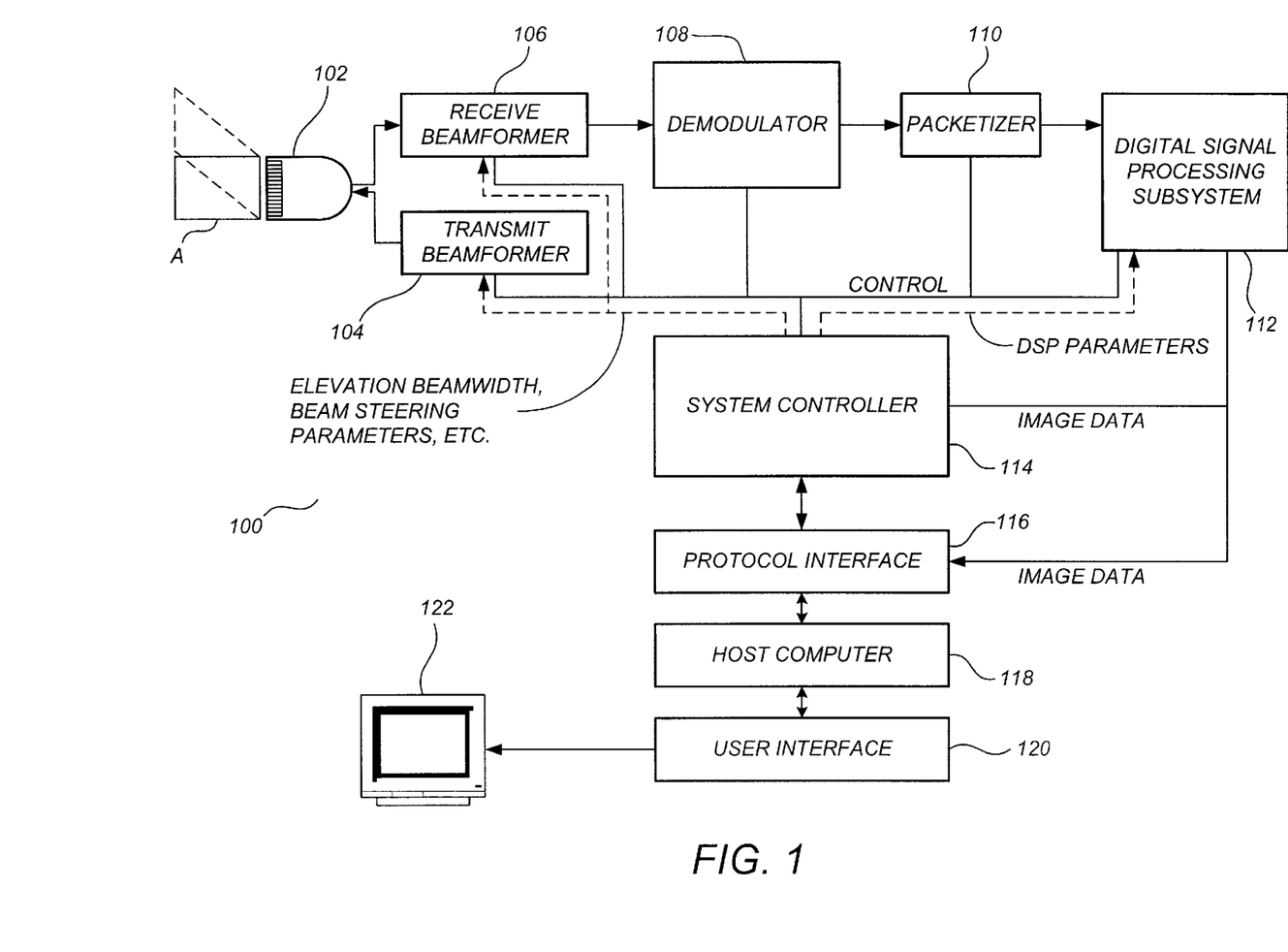
FIG. 1 illustrates a functional block diagram of an ultrasound system according to a preferred embodiment.

FIG. 1 illustrates a block diagram of an ultrasound imaging system 100 in accordance with a preferred embodiment. Ultrasound imaging system 100 comprises a transducer 102, a transmit beamformer 104, a receive beamformer 106, a demodulator 108, a packetizer 110, a digital signal processing (DSP) subsystem 112, a system controller 114, a protocol interface 116, a host computer 118, a user interface 120, and a display 122. Although many ultrasound system architectures may be readily adapted for use in accordance with the preferred embodiments, ultrasound imaging system 100 is preferably similar to the those described in the commonly assigned U.S. Ser. No. 09/224,635, filed Dec. 31, 1998, U.S. Ser. No. 09/449,095 filed Nov. 24, 1999, and U.S. Ser. No.

09/721,889 filed Apr. 1, 2001, which are incorporated herein by reference, or to the ultrasound imaging system currently named the USI-2000™ available from U-Systems, Inc. of San Jose, Calif. These ultrasound imaging systems have been found particularly suitable for implementing biopsy needle enhancement according to the preferred embodiments because their modular, scalable, and flexible architectures readily allow different sets of transmit parameters, receive parameters, and frame processing parameters to be dynamically assigned on a per-frame basis. Thus, these systems are readily adaptable for generating (i) an ordinary frame, directed to imaging the target region tissues, according to a first set of parameters, and immediately thereafter generating (ii) a special purpose frame, directed to imaging the biopsy needle, according to a second set of parameters different than the first set of parameters.

Transducer 102 comprises an array of transducer elements that transmits focused acoustic signals into a target responsive to signals generated by the transmit beamformer 104. In a preferred embodiment, transducer 102 transmits acoustic pulses into an area A that is relative to the transducer, the pulse parameters and orientation of area A being different for ordinary ultrasound frames than for special purpose frames. Responsive to control signals and parameters received from system controller 114, including elevation beamwidth parameters, beam steering parameters, and other parameters, transmit beamformer 104 generates signals that are converted into acoustic interrogation signals by transducer 102 and introduced into the target. Transducer 102 also receives acoustic echoes from the target and converts them into signals for forwarding to receive beamformer 106. Receive beamformer 106 receives the signals and converts them into a single-channel RF signal, also doing so in accordance with elevation beamwidth parameters, beam steering parameters, and other parameters provided by system controller 114.

Demodulator 108 receives the single-channel RF signal and generates component frames therefrom, which are then packetized by packetizer 110 and fed to DSP subsystem 112. In accordance with control signals and parameters received from system controller 114 that dictate the one-, two-, and/or three-dimensional signal processing functions required, DSP subsystem 112 continuously generates processed images corresponding to the ordinary frames and special purpose frames, including compound images resulting from predetermined combinations of the ordinary and special purpose frames. The output image data is transferred to protocol interface 116, but may optionally be further processed by system controller 114. The compound output image frames are then transferred to host computer 118 which performs scan conversion on the signals for transmission to user interface 120 and ultimate display by display 122.

It is to be appreciated that while one particularly suitable ultrasound system is disclosed supra, biopsy needle visualization enhancement according to the preferred embodiments may be carried out using any of a variety of types of ultrasound hardware and software. Given the present disclosure, those skilled in the art will be readily able to implement ultrasound system hardware and software configurations capable of achieving the functionalities described herein.

Figure 2A:
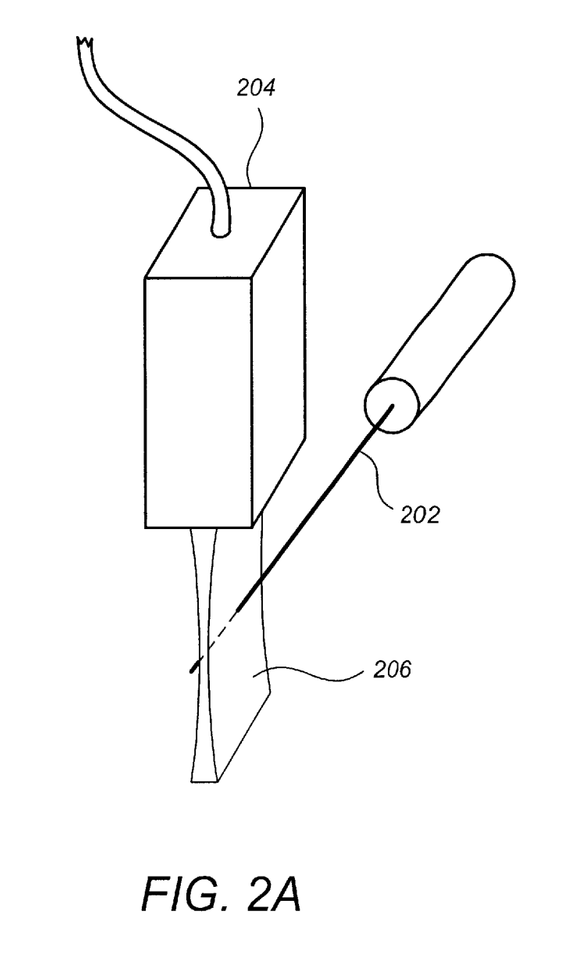
FIGS. 2A and 2B illustrate ultrasound elevation beam widths corresponding to an ordinary ultrasound frame and a special purpose ultrasound frame, respectively, in accordance with a preferred embodiment.
Figure 2B:
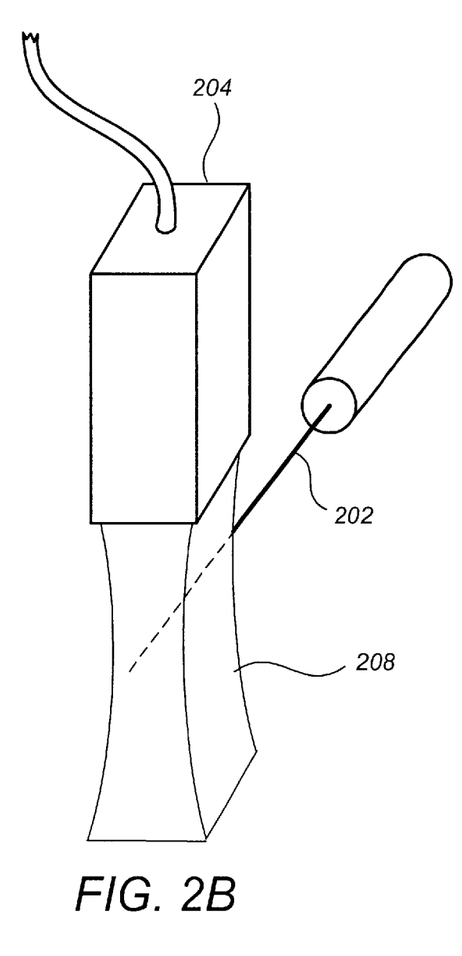

FIGS. 2A and 2B illustrate ultrasound elevation beam widths corresponding to an ordinary ultrasound frame and a special purpose ultrasound frame, respectively, in accordance with a preferred embodiment. Shown in FIG. 2A is a biopsy needle 202 positioned with respect to an ultrasound probe 204. An ordinary frame slice 206, corresponding to a coverage volume of an ordinary ultrasound frame, extends downward from the ultrasound probe 204 in the plane thereof. For simplicity and clarity of explanation, the biopsy needle 202 in the example of FIG. 2A is almost parallel to the transducer array of the ultrasound probe 204, the non-parallel case being described further infra. However, as often happens during biopsy procedures, the biopsy needle 202 is slightly out-of-plane with respect to the ordinary frame slice 206.

Because ordinary frames are intended for the optimal imaging of target tissue, including the lesion that is the object of the biopsy procedure, the ordinary frame slice 206 is generally narrow in the elevation direction (i.e., the left-to-right direction in FIG. 2A). This is because as the elevation beam width increases, an averaging effect occurs in the elevation direction and the output ultrasound image has less clarity as compared to ultrasound images generated with thinner elevation beam widths. Disadvantageously, however, when the position of the biopsy needle 202 is slightly out-of-plane with respect to the ordinary frame slice 206, as in the case of FIG. 2A, it only intersects that slice for a brief interval. Accordingly, if only ordinary frames were used, much of the biopsy needle 202 of FIG. 2A would not appear on the output display.

According to a preferred embodiment, because so much information is already known about the biopsy needle 202, it is not required that the biopsy needle 202 be imaged using the thin, high-resolution slices of the ordinary frames. Rather, it is more important to capture as much of the biopsy needle as possible, albeit at a lesser resolution, then it is to capture smaller portions of the biopsy needle at the same high resolution as the target lesion. This is especially true because much information about the biopsy needle is already known (e.g., it is narrow and straight), and so the image of the biopsy needle 202 is highly amenable to digital signal processing techniques to sharpen and enhance it prior to display. Moreover, even if little or no digital signal processing techniques are applied and the needle image is slightly out of focus on the output display, this display can still be more useful to the user than a display which shows a clearer, but very small, portion of the biopsy needle.

Accordingly, shown in FIG. 2B is a special purpose frame slice 208 that is substantially wider in the elevation direction then the ordinary frame slice 206. According to a preferred embodiment, the special purpose frames are received, are optionally digitally enhanced, and are compounded with ordinary frames for output to a display monitor. The special purpose frames are transmitted and received according to special purpose frame parameters the dictate the elevation beam width, focus, steering angle, and other parameters. Importantly, successive special purpose frames are not necessarily required to have the same parameters. For example, it may be advantageous to alternate between two types of special purpose frames having different elevation beam widths, e.g., one type having an elevation beamwidth twice the ordinary frame elevation beam width, and another type having an elevation beamwidth three times the ordinary frame elevation beam width. Moreover, the special purpose frame parameters may very dynamically. For example, they may vary their steering parameters dynamically according to the current orientation of the biopsy needle 202, as described further infra. By way of notation, a $k^{th}$ set or vector of special purpose frame parameters will be denoted SPP(k) herein. Where there are N vectors of special purpose frame parameters, they can accordingly be contained in a N-vector array SPP(N). Advantageously, in addition to having wider elevation beam widths than the ordinary frames, the special purpose frames may also be steered to impinge upon the needle at an increased angle, and can be laterally focused on a line-by-line basis to the needle depth, as will be described further infra with respect to FIGS. 4A and 4B.

Any of several methods known in the art may be used to adjust the elevation beam width of the special purpose frames. For 1-D transducer arrays containing only a single row of transducer elements, the elevation beam width can be increased by reducing the operating frequency. By way of example and not by way of limitation, because the elevation beam width is generally inversely proportional to the operating frequency, a reduction of the operating frequency from 7 MHz to 5 MHz can increase the elevation beam width by about 30 percent. For "1.5-D" and 2-D transducer arrays management of the elevation aperture is an additional method of increasing the elevation beam width. By way of example and not by way of limitation, the "F-number" for the transducer array can be increased to increase the elevation beam width. Doubling the "F-number" will usually double the elevation beam width at each depth, and will have the further advantage of quadrupling the depth of focus in the elevation direction. By way of further example, an elevation beamwidth aperture apodization window, such as a Hamming window, may be used to make the effective aperture narrower, thereby increasing the elevation beam width.

Any of a variety of compounding algorithms may be used in accordance with the preferred embodiments. For example, a simple compound image comprising two frames, one ordinary frame compounded with one special purpose frame, could be output to the display. Alternatively, a different number of special purpose frames could be associated and compounded with a single ordinary frame. Even further, more than one ordinary frame may be compounded together with a single special purpose frame which could, for example, yield the additional benefit of speckle reduction in addition to needle visualization enhancement. According to one preferred embodiment, the image re-registration portion of the image compounding algorithms may be carried out using a $0^{th}$ order interpolation algorithm, as opposed to a bilinear or other more complicated interpolation algorithm, for further reducing the processing time and increasing the frame rate. This has been found to yield good results because, as discussed supra, "perfection" is not necessarily required in displaying the biopsy needle. It is the biopsy needle's position and orientation, and not its visual features, that are of primary importance to the medical professional during the biopsy procedure.

Figure 8:
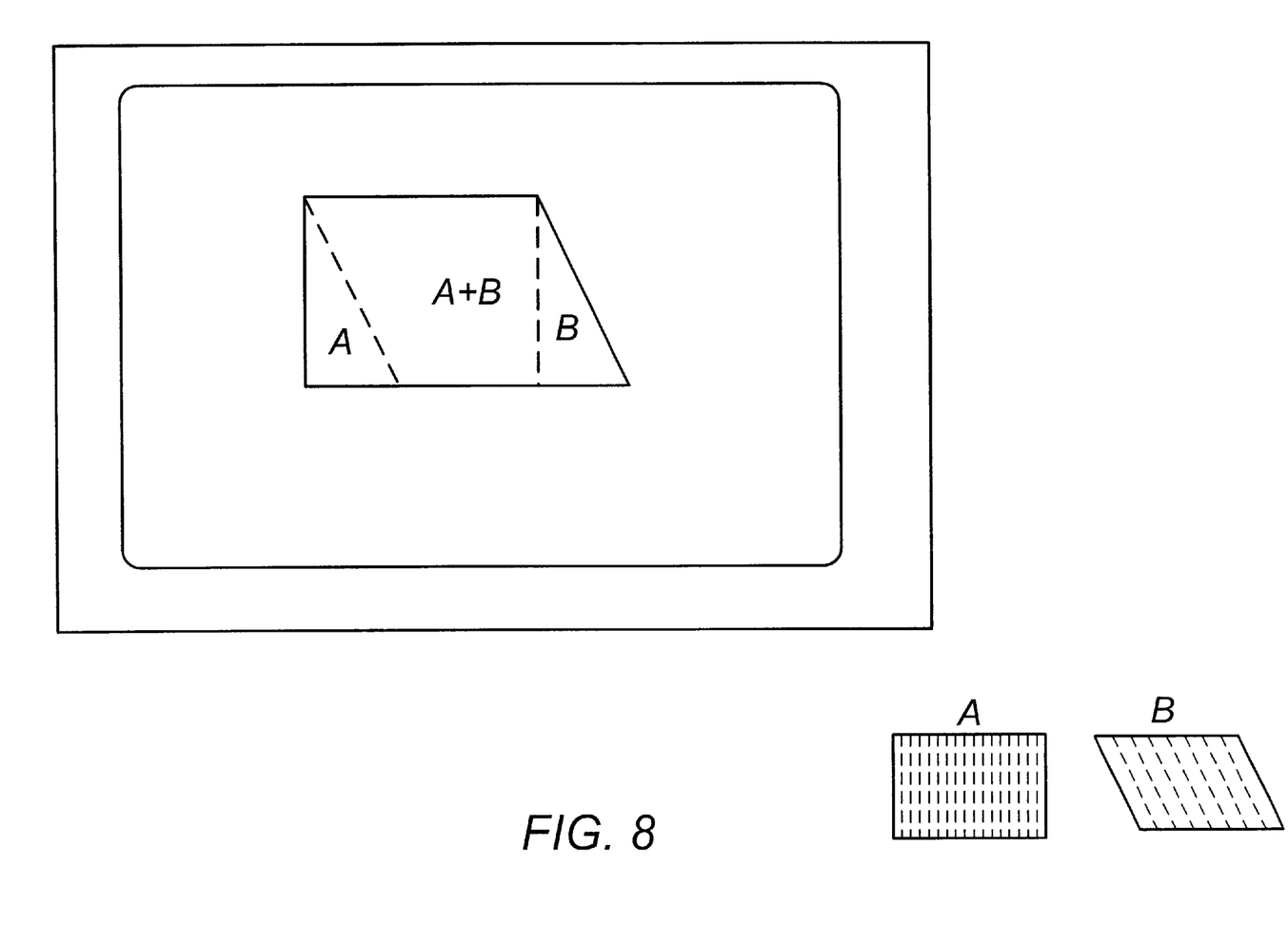
FIG. 8 illustrates an example of an output image in accordance with a preferred embodiment.

For cases in which the special purpose frame angles are different than the normal angle of the ordinary frames, an additional section having a right-triangular shape will be appended to the normally-rectangular output image e.g., as illustrated in FIG. 8. The resulting novel output image is half-trapeziodal in shape, comprising a rectangular portion containing the ordinary frame information (A), and as enhanced by the special purpose frame information (A+B), and a right-triangular portion (B) containing only the special purpose frame information. In addition to containing the imaged biopsy needle, the right-triangular portion may also comprise an appreciable amount of target image information depending on the digital signal processing algorithms that were used to highlight the needle, suppress clutter, etc.

Any of a variety of digital signal processing algorithms may be used in accordance with the preferred embodiments on the special purpose frames and/or the ordinary frames. In one embodiment, needle enhancement algorithms are performed on the special purpose frames, while lesion enhancement algorithms are performed on the ordinary frames, with both the biopsy needle and the target lesion being enhanced on the output display. For example, the needle can be highlighted with a first color and/or brightness level, while the lesion can be highlighted with a second color and/or the border of the lesion can be circumscribed in a highlighted color. In another embodiment, only the needle is enhanced and highlighted on the display. The needle enhancement algorithms may include, but are not limited to, low-pass filtering, thresholding, edge enhancement, contrast enhancement, and other algorithms.

As an alternative or addition to being enhanced using convolution-style image processing algorithms, straight-line-seeking image segmentation algorithms may be used to identify the biopsy needle in terms of a point-slope equation or other form of abbreviated identification that is more efficient than a bitmap-type representation. Substantial time can be saved by mapping only those image elements associated with the biopsy needle onto the ordinary frames prior to display. Segmentation algorithms and other digital signal processing algorithms can be found, for example, in Gonzalez, *Digital Image Processing*, Addison-Wesley Publishing Co. (1992), which is incorporated by reference herein. Lesion detection algorithms can be found, for example, in Cheng, X. Y.; Akiyama, I.; Itoh, K.; Wang, Y.; Taniguchi, N.; Nakajima, M., "Automated Detection of Breast Tumors in Ultrasonic Images Using Fuzzy Reasoning," Proceedings of the International Conference on Image Processing, Volume III, pp. 420–423, IEEE Computer Society (Oct. 26–29, 1997), and Cheng, Xiangyong, A Study on Automated Extraction of Breast Tumors Using Three Dimensional Ultrasonic Echography, Ph.D. Thesis, Keio University, Japan (1997), which are incorporated by reference herein.

According to one preferred embodiment, the user can choose at any time from among three different modes for carrying out biopsy needle visualization enhancement. As will be discussed further infra with respect to FIGS. 5A and 5B, an adaptive mode automatically detects the position of the needle with respect to the probe, in terms of both an angle $\theta$ and a depth $d_0$, and automatically steers the beam toward the needle. In a user steered mode, the user may directly manipulate the steering angle $\theta$ of the special purpose frame beams, and may optionally input the needle depth $d_0$ as well. This can be done using a trackball, keyboard input, or other input means. In a simple mode, a small set of steering angles is preselected by the user using an intuitive, easy-to-use interface, the ultrasound system toggles among these steering angles in successive special purpose frames.

All three of the above modes (adaptive, user steered, and simple) may provide enhanced biopsy needle viewing resulting from increased elevation beam width, in accordance with the preferred embodiment described supra. However, each of these modes offers relative advantages and disadvantages with respect to each other, and the user may advantageously select among these modes for the purpose at hand. For example, while the adaptive mode is easy-to-use and yields good imaging results by automatically steering and laterally focusing the ultrasound beam, the overall output frame rate may generally be higher in the user steered mode. As another example, while the simple mode is easiest to use, it may also have a slower frame rate than the user steered mode as the number of preselected angles increases.

Figure 3:
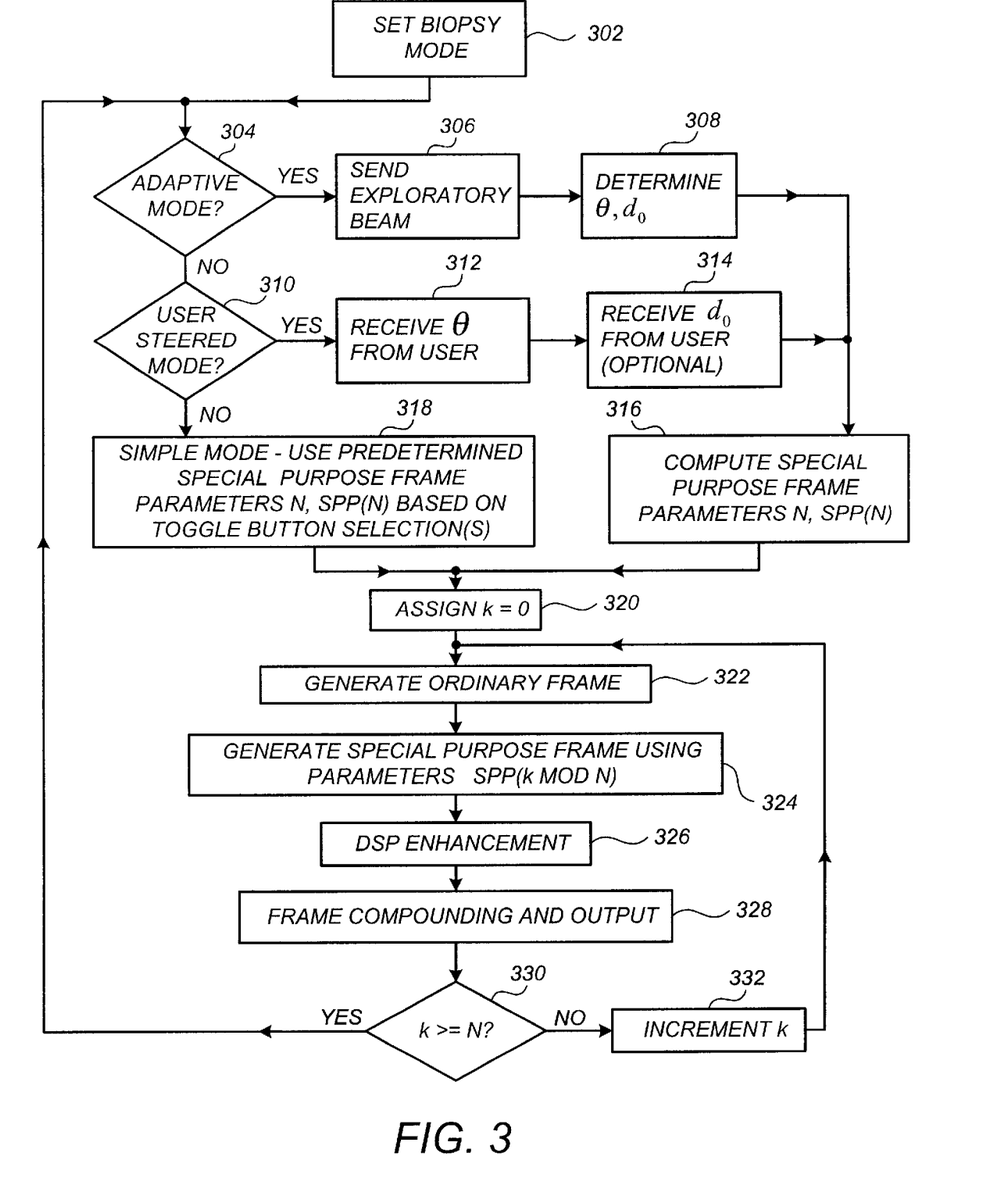
FIG. 3 illustrates steps for enhancing needle visualization according to a preferred embodiment.

FIG. 3 illustrates steps for enhancing needle visualization according to a preferred embodiment. At step 302, the user causes the system to enter a biopsy mode. At step 304, it is determined whether an adaptive mode has been selected by the user, and if so, at steps 306 and 308 an exploratory beam is swept across the target region and the needle position parameters θ and $d_0$ are determined using the preferred method described infra with respect to FIGS. 5A and 5B. At step 316, special purpose frame parameters N and SPP(N) are computed according to the detected values for θ and $d_0$. As an alternative embodiment to the exploratory beam method, position sensors may be attached to the probe and to the needle and the needle angle and depth may be determined from position sensor readings.

If the system is in a user steered mode (step 310), the values for θ and (optionally) $d_0$ are received from the user and the special purpose frame parameters N and SPP(N) are computed therefrom. If neither the adaptive mode nor the user steered mode is being used, then at step 318 a set of predetermined simple mode parameters N, SPP(N) are used according to the simple-mode user interface buttons that the user has engaged.

At step 320, a counter variable k is set to 0. At step 322, and ordinary frame is generated. At step 324, a special purpose frame is generated using the $k^{th}$ set of special purpose frame parameters SPP(k). At step 326, DSP enhancement procedures are performed on the ordinary frame and/or the special purpose frame. At step 328, frame compounding and output are performed. At step 330, if the number of special purpose parameter sets N has been reached, the algorithm continues again at step 304. If not, then k is incremented and the next ordinary frame is generated at step 322.

Many variations of the ordering of the above steps may be used according to the preferred embodiments. For example, although θ and $d_0$ are only updated after every "N" special purpose frames in the embodiment of FIG. 3 (representing one cycle through the "N" sets of different parameters), in another preferred embodiment these values may be refreshed for every special purpose frame. Additionally, many variations in the nature and timing of frame compounding are within the scope of the preferred embodiments.

Figure 4A:
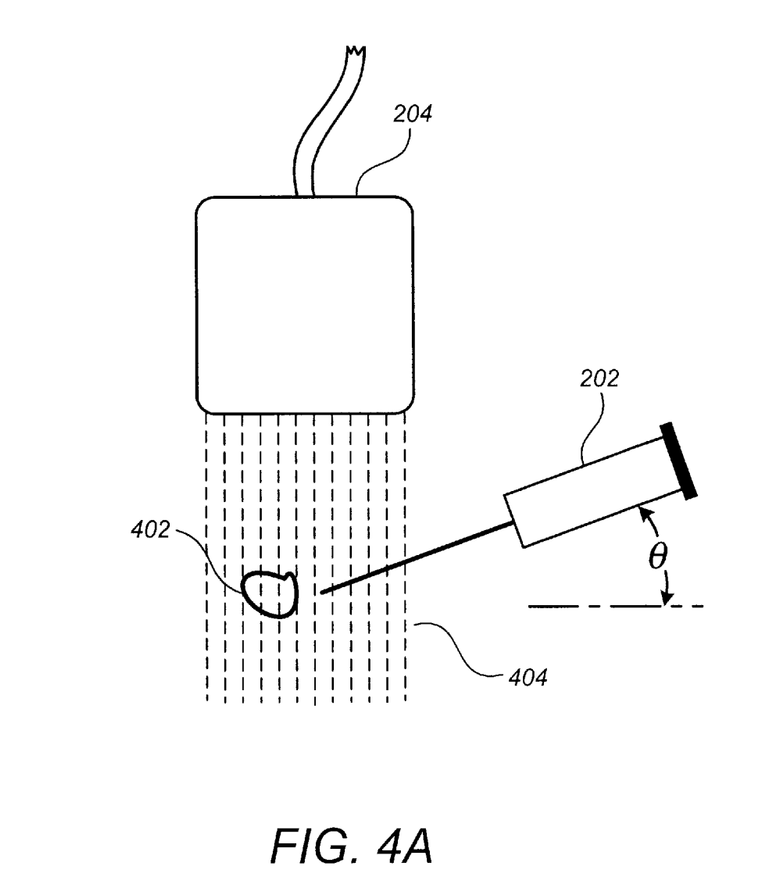
FIGS. 4A and 4B illustrate ultrasound probe, biopsy needle, and scan line positions and orientations corresponding to an ordinary frame and a special purpose frame, respectively, in accordance with a preferred embodiment.

FIGS. 4A and 4B illustrate ultrasound probe, biopsy needle, and scan line positions and orientations corresponding to an ordinary frame and a special purpose frame, respectively, in accordance with a preferred embodiment. Shown in FIG. 4A is the biopsy needle 202 positioned at an angle θ with respect to the transducer surface of ultrasound probe 204. Ordinary frame scan lines 404 impinge upon the biopsy needle 202 at an angle of θ degrees from the perpendicular. Generally speaking, the ordinary frame scan lines 404 will be closely spaced in the lateral direction to optimize the image resolution of the target lesion 402. The elevation beamwidth associated with the ordinary frame of FIG. 4A is shown in FIG. 2A. It has been found that variations of the angle of incidence of the scan lines from the perpendicular to the biopsy needle 202 beyond about 8 degrees will often cause substantial degradation in the image quality of the biopsy needle. Accordingly, if only ordinary frames were used on the output display and the angle θ was in excess of about 5 to 8 degrees, needle image quality would suffer substantially.

Figure 4B:
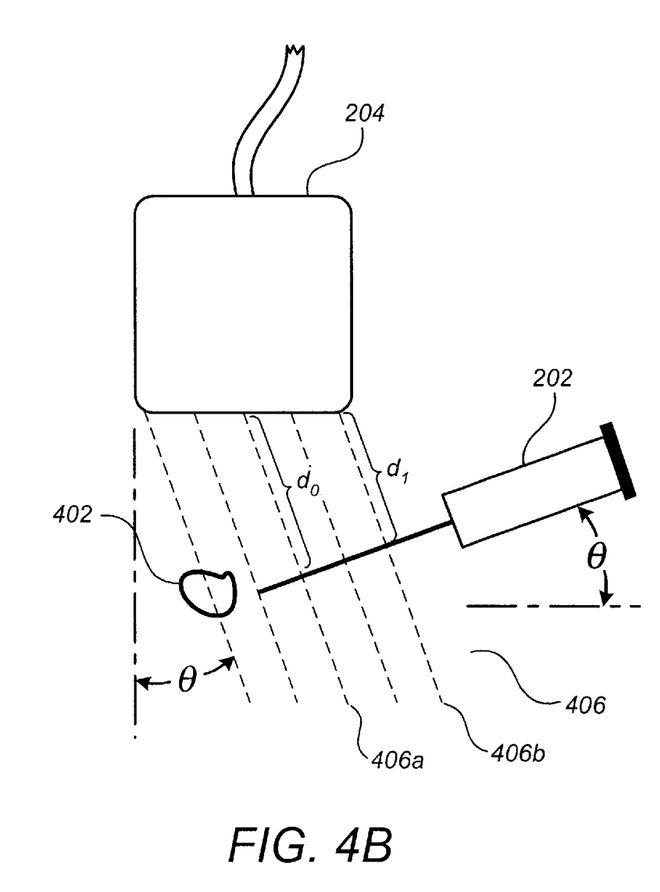

Shown in FIG. 4B are the biopsy needle 202 and ultrasound probe 204 during a special purpose frame, whose scan lines are shown as elements 406. Special purpose frame scan lines 406 impinge upon the biopsy needle 202 at a 90 degree angle. Where 90 degree angles are not achievable, this angle is as close as practicable to a 90 degree angle. In accordance with a preferred embodiment, the lateral focusing of special purpose frame scan lines 406 is performed on a per-scan-line basis. In particular, successive scan lines are laterally focused at different depths corresponding to the differing distances between the transducer array and the biopsy needle at different points along the transducer array. These differing distances are graphically depicted in FIG. 4B, in which the transducer array is separated from the biopsy needle by a distance $d_0$ along a first scan line 406a near the center of the transducer array, the separation is a shorter distance $d_1$ along a second scan line 406b near the edge of the transducer array. Thus, according to the preferred embodiment, the scan line 406a is laterally focused at the depth $d_0$, while the scan line 406b is laterally focused at the depth $d_1$, and likewise-computed lateral focus depths are assigned for all of the special purpose frame scan lines 406. The elevation beam width associated with the special purpose frame of FIG. 4B is shown in FIG. 2B.

As indicated by the wider spacing of the special purpose frame scan lines 406 in FIG. 4B, the number of scan lines for the special purpose frames may be reduced without substantial reduction in needle image quality. Because the biopsy needle shape is predictably straight, it has been found that needle image quality does not appreciably deteriorate even when the number of scan lines is decreased by 50 percent or more from the number of scan lines in the ordinary image. This leads to a substantial savings in processing time and a corresponding increase in overall frame rate.

Figure 5A:
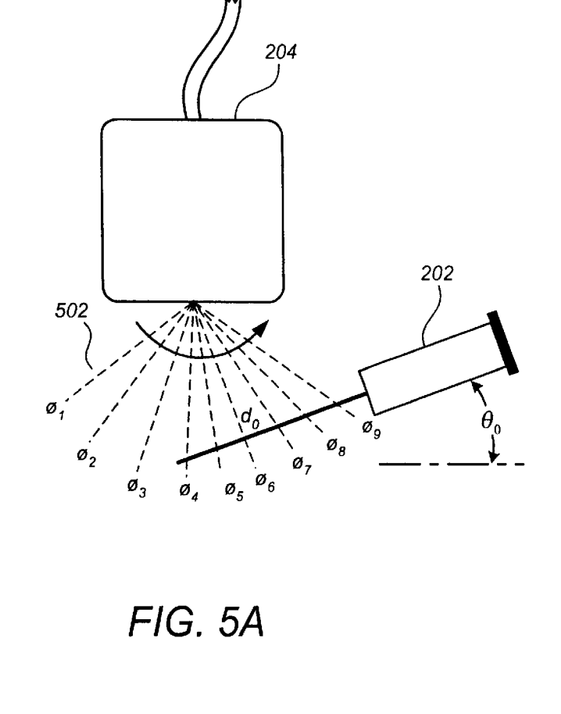
FIGS. 5A and 5B illustrate an exploratory ultrasound beam and echoes corresponding thereto, respectively, during an adaptive needle position detection process in accordance with a preferred embodiment.
Figure 5B:
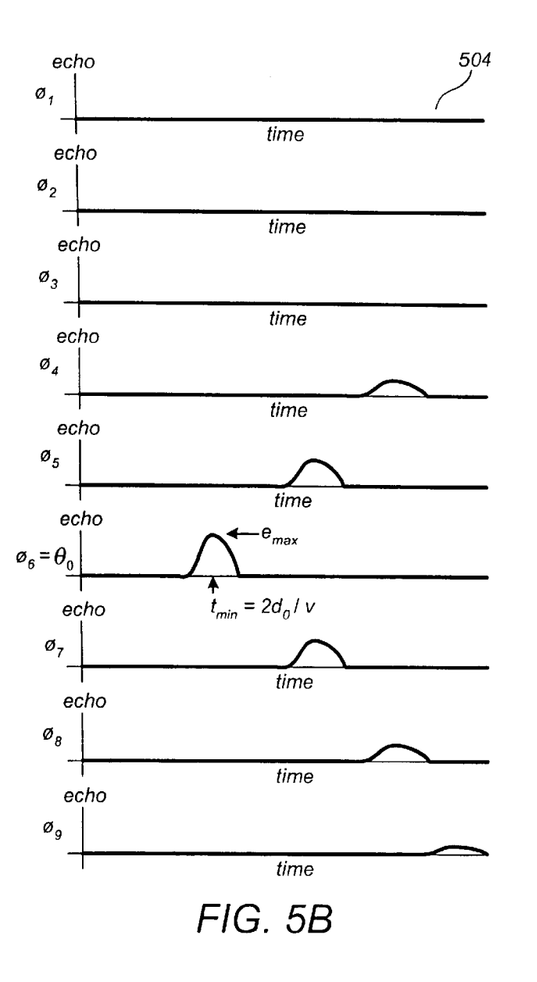

FIGS. 5A and 5B illustrate an exploratory ultrasound beam 502 and echo signals 504 therefrom, respectively, during an adaptive needle position detection process in accordance with a preferred embodiment. At periodic or nonperiodic intervals sufficient to keep up with a moving needle, an exploratory beam is fired along the direction $\phi_1$, then $\phi_2$, then $\phi_3$, etc., as shown in FIG. 5A, until a large arc is subtended. The exploratory pulses sent along directions that do not intersect the biopsy needle 202 are not reflected, whereas exploratory pulses sent along directions to do intersect the needle are reflected back. Those exploratory pulses that are reflected back will be measured with delay times and strengths that reflect the closeness to the needle, and the incidence angle with the needle, along the pulse direction. As indicated in FIG. 5B, the strongest and closest reading at $\phi_6$ corresponds to the angle $\theta_0$ of the needle, as well as the distance $d_0$ to the needle according to the relation $t_{min}=2d_0/v$, where v is the velocity of sound in the target tissue. Any of a variety of algorithms may be used to select among the signal echoes to determine $\theta_0$ and $d_0$. In one preferred embodiment, this algorithm simply chooses the angle φ corresponding to the earliest reflection. More processing may be done to overcome the effects of noise, clutter, etc., in determining the needle angle and distance (e.g., low pass filtering, verifying that the earliest returned pulse corresponds to the largest-magnitude returned pulse, etc.).

Figure 6:
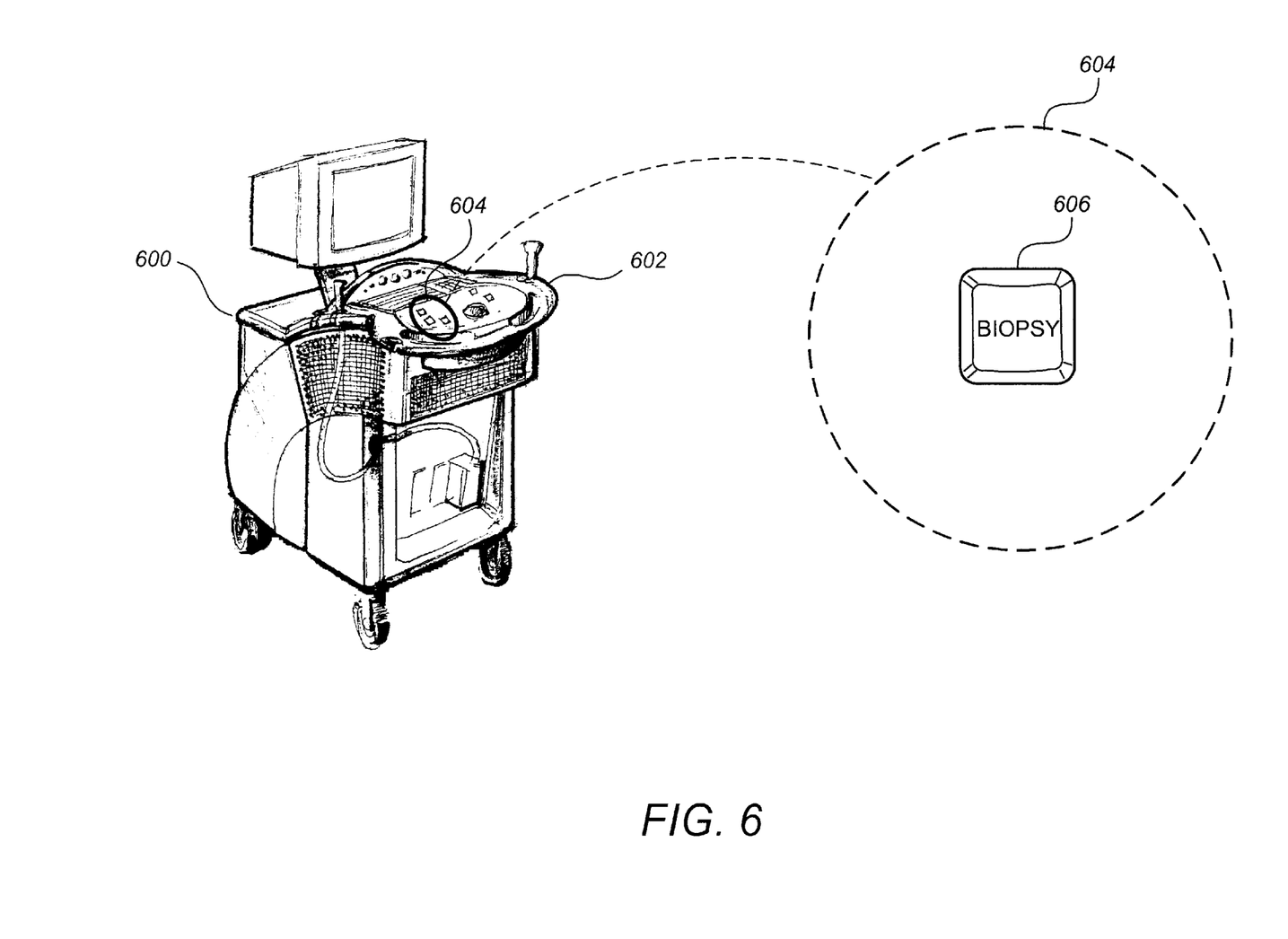
FIG. 6 illustrates a user interface for biopsy needle visualization in accordance with a preferred embodiment.

FIG. 6 illustrates a user interface 604 for biopsy needle visualization in accordance with a preferred embodiment, as incorporated into an ultrasound system 600 having an overall user interface 602. In this simplest preferred embodiment, a single "biopsy" key 606 is provided to the user that toggles among different states. One set of states is presented here by way of nonlimiting example. In a first state, the biopsy feature is disabled. After pressing the biopsy key 606 once, a second state is entered, wherein a predetermined number (in particular, N=3) of special purpose frames are successively compounded with ordinary frames, and wherein the special purpose frame parameters SPP(1), SPP(2), and SPP(3) have lateral beam steering angles of −15 degrees, 0 degrees, and +15 degrees, respectively. Preferably, each of the special purpose frame parameters SPP(1), SPP(2), and SPP(3) also has an elevation beam width that is greater than the elevation beam width of the ordinary frames.

If the biopsy key 606 is pressed again, a third state is entered in which only one special purpose frame is compounded with ordinary frames, wherein the steering angle of this one special purpose frame is equal to +15 degrees. If the biopsy key 606 is pressed again, a fourth state is entered in which this angle changes to 0 degrees. If the biopsy key 606 is pressed again, a fifth state is entered and this angle changes to −15 degrees. Finally, biopsy key 606 is pressed again, the system returns to the first state. While the above parameters are presented by way of example to clearly illustrate a preferred embodiment, it is to be appreciated that a wide variety of predetermined parameters may be used without departing from the scope of the preferred embodiments.

Figure 7:
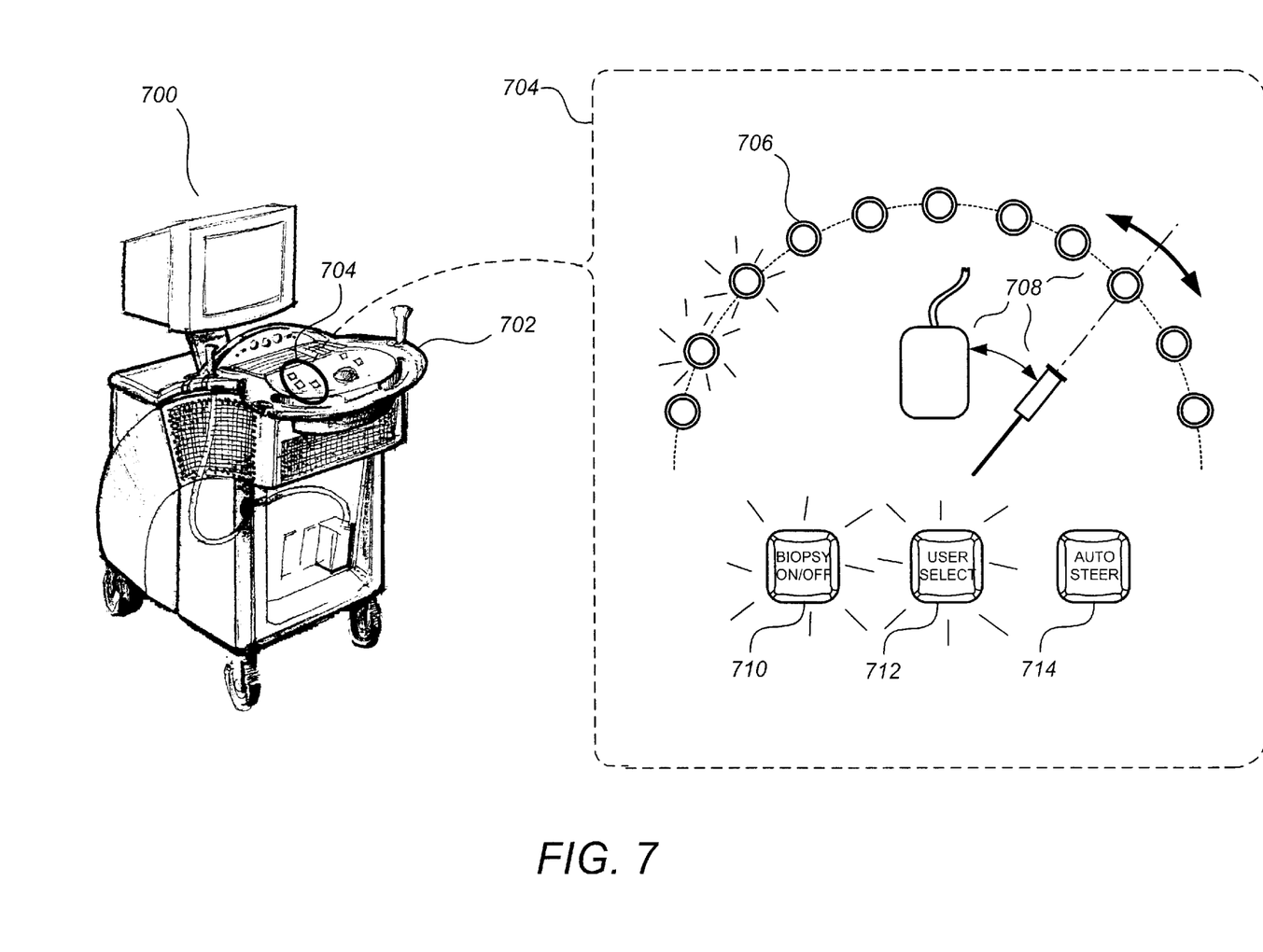
FIG. 7 illustrates another user interface for biopsy needle visualization in accordance with a preferred embodiment.

FIG. 7 illustrates a user interface 704 for biopsy needle visualization in accordance with a preferred embodiment, as incorporated into an ultrasound system 700 having an overall user interface 702. A plurality of needle angle buttons 706 are provided in a semicircular arrangement around an explanatory diagram 708 that clearly illustrates their purpose. Each of the needle angle buttons 706 is a toggle button having an ON state and an OFF state, the ON state causing the key to be backlighted. When a given needle angle button 706 is ON, a special purpose frame having a steering angle corresponding to the direction indicated by that needle angle button is activated. In particular, the steering angle is perpendicular to, or as close as perpendicular as practicable to, a needle direction indicated by an imaginary line running from that needle angle button to the center of the semicircle formed by the needle angle buttons 706. For each ON button, the number of special purpose frame parameter sets "N" is incremented by one, and one additional set of parameters is added to the special purpose frame parameters SPP(N). Successive special purpose frame parameter sets SPP(k) are cycled through corresponding to the number of ON buttons, and a compound image is formed from the ordinary image and the "N" special purpose frames. The user may have as many ON buttons as they like, with the understanding that greater angular coverage resulting from additional ON buttons will also reduce the overall frame rate. In the example of FIG. 7, the user has selected two needle angle buttons 706 corresponding to −45 and −60 degrees. Accordingly, there are two different special purpose frame parameters SPP(1) and SPP(2) interleaved between ordinary frames and steered such that they would normally impinge upon needles oriented at −45 and −60 degrees, respectively. In another preferred embodiment, each special purpose frames may be separately compounded with neighboring ordinary frames as they are generated, in which case the frame rate will not decrease as the number of ON buttons is increased.

The overall scheme represented by needle angle buttons 706 is activated by a USER SELECT key 712, as shown in FIG. 7. At any time, the user may switch into the adaptive mode, in which the biopsy needle angle and distance are automatically and adaptively detected, by pressing an AUTO STEER key 714. The overall biopsy needle visualization enhancement mode is entered and exited by pressing the BIOPSY ON/OFF key 710.

According to a preferred embodiment, needle angle buttons 706 have angular spacings from each other no greater than a predetermined critical angle. In a particular preferred embodiment, this critical angle is about 10 to 16 degrees such that, when the proper needle angle buttons are selected, the steering angle of the special purpose frames is never greater than 5 to 8 degrees, respectively, away from the optimal 90 degree angle of incidence with the biopsy needle. As described supra, the image quality of the biopsy needle begins to decrease drastically when this angle is greater than about 5 to 8 degrees. In the embodiment of FIG. 7, the needle angle buttons 706 are placed about 15 degrees apart.

Many variations of the user interface 704 of FIG. 7 are within the scope of the preferred embodiments including, without limitation, virtual-type user interfaces in which the buttons are actually icons on a user display that are clicked and unclicked using a mouse (see, e.g., U.S. Pat. No. 6,063,030, which is incorporated by reference herein). It is to be appreciated that special purpose frames, while containing parameters directed to optimizing biopsy needle viewing, will often provide at least some useful imaging information regarding the lesion. This at least partially offsets the decreases in the ordinary frame rate brought about by the insertion of special purpose frames into the imaging process, as the inserted frames may also add useful information regarding the lesion.

In an additional preferred embodiment, the special purpose frame beams are steered in the elevation direction is addition to the lateral direction, such that they have an increased angle of incidence to the needle with respect to the elevation direction as well. This preferred embodiment requires the use of 2-D ultrasound probes that, as known in the art, are capable of beam steering in the elevation direction as well as in the lateral direction. Upon segmentation, the needle may be then be projected onto the plane of the ultrasound slice 3-dimensional projection algorithm.

Whereas many alterations and modifications of the present invention will no doubt become apparent to a person of ordinary skill in the art after having read the foregoing description, it is to be understood that the particular embodiments shown and described by way of illustration are in no way intended to be considered limiting. For example, while presented supra in the context of breast lesion biopsy procedures, the preferred embodiments are readily applicable to any type of ultrasound-guided medical procedure in which a specular instrument needs to be imaged. Even further, the preferred embodiments may be readily extended to any of a variety of ultrasound-guided activities, be they medical or non-medical, in which a specular instrument needs to be imaged as it is manipulated beneath a surface or inside a cavity. Moreover, although presented supra in the context of B-mode imaging, the preferred embodiments are readily applied to color flow mode, power Doppler mode, or other two- or three-dimensional ultrasound imaging modes. Therefore, reference to the details of the preferred embodiments are not intended to limit their scope, which is limited only by the scope of the claims set forth below.

What is claimed is:

1. A method for generating an ultrasound display of a target region into which a specular reflector is inserted, comprising the steps of:

generating a first frame according to a first set of frame parameters directed to the imaging of the target region;

generating a second frame according to a second set of frame parameters directed to the imaging of the specular reflector;

modifying said first frame with information from said second frame relating to a location and orientation of the specular reflector; and displaying an output image derived from said modified first frame;

wherein said first and second sets of frame parameters are selected such that an elevation beam width of said second frame is greater than an elevation beam width of said first frame.

2. The method of claim 1, wherein said step of modifying said first frame with information from said second frame comprises the step of compounding said first frame with said second frame.

3. The method of claim 2, further comprising the step of digitally enhancing said second frame to highlight the specular reflector prior to said compounding step.

4. The method of claim 3, said specular reflector being inserted into the target region as part of a medical procedure in which the specular reflector is required to approach a lesion in the target region, further comprising the step of digitally enhancing said first frame to highlight the lesion prior to said compounding step.

5. The method of claim 1, wherein said first and second sets of frame parameters are selected such that said second frame comprises fewer scan lines than said first frame.

6. The method of claim 1, wherein said first and second sets of frame parameters are selected such that scan lines associated with said second frame are incident upon the specular reflector at an angle that is closer to a normal direction as compared to a corresponding scan line incidence angle for said first frame.

7. The method of claim 6, said first and second frames being generated from ultrasonic beams generated by an ultrasound probe having an array of transducers thereon, said specular reflector forming a first angle with respect to said transducer array, wherein said second set of frame parameters is computed to steer the scan lines associated with said second frame at a steering angle with respect to an axis of the ultrasound probe, and wherein said steering angle is closer to said first angle than a corresponding scan line angle associated with said first frame.

8. The method of claim 7, wherein said first angle and said steering angle are fixed at a predetermined value.

9. The method of claim 7, wherein said first angle varies depending on a manual positioning of the specular reflector and the ultrasound probe by a user, and wherein said first angle is determined using position sensing equipment affixed to said specular reflector and to said ultrasound probe, respectively, for allowing dynamic computation of said steering angle.

10. The method of claim 7, wherein said first angle varies depending on a manual positioning of the specular reflector and the ultrasound probe by a user, and wherein said first angle is automatically measured by performing the steps of:

sweeping a series of exploratory ultrasound pulses across a range of angles in said target region; and using echoes corresponding to said exploratory ultrasound pulses to compute a measure of said first angle;

wherein said steering angle is dynamically computed based on said measure of said first angle.

11. The method of claim 7, wherein lateral focusing depths associated with respective scan lines of said second frame vary on a per-scan-line basis, according to a varying distance along each scan line between the transducer array and the specular reflector.

12. The method of claim 1, wherein said specular reflector comprises a biopsy needle.

13. A simplified user interface apparatus for receiving user inputs that dictate enhanced biopsy needle visualization parameters in an ultrasound system, the enhanced biopsy needle visualization parameters including a state identifier that identifies one of a plurality of needle enhancement modes, said apparatus comprising a single key that toggles among said plurality of needle enhancement modes upon actuation by the user, wherein said plurality of needle enhancement modes comprises a first mode in which needle enhancement is deactivated and a second mode in which a first needle enhancement frame steered at a first fixed steering angle is compounded with an ordinary frame and output to a display.

14. The simplified user interface apparatus of claim 13, wherein said plurality of needle enhancement modes further comprises a third mode in which a first needle enhancement frame steered at said first fixed steering angle and a second needle enhancement frame steered at a second fixed steering angle are compounded with an ordinary frame and output to the display.

15. The simplified user interface apparatus of claim 14, wherein said plurality of needle enhancement modes further comprises a fourth mode in which a first needle enhancement frame steered at said first fixed steering angle, a second needle enhancement frame steered at said second fixed steering angle, and a third needle enhancement frame steered at a third fixed steering angle are compounded with an ordinary frame and output to a display.

16. A simplified user interface apparatus for receiving user inputs that dictate enhanced biopsy needle visualization parameters in an ultrasound system, the enhanced biopsy needle visualization parameters including one or more biopsy needle angles for which special purpose needle detection frames are to interrogate a target region, said apparatus comprising an array of ON/OFF buttons spatially arranged such that each ON/OFF button spatially emulates an angle at which a biopsy needle is oriented with respect to an ultrasound probe, wherein said biopsy needle angle parameters are determined at any given time by a number and orientation of those ON/OFF buttons that are in an ON state.

17. The simplified user interface of claim 16, wherein said array of ON/OFF buttons forms a semicircular pattern around an explanatory icon, said explanatory icon comprising a representation of an ultrasound probe and a biopsy needle positioned at an angle thereto.

18. The simplified user interface of claim 16, wherein the number and positioning of said ON/OFF buttons is such that said ON/OFF buttons correspond to biopsy needle angles separated by not greater than two times a critical angle of the ultrasound system being used, said critical angle corresponding to an angular deviation of an ultrasound beam from a perpendicular to a biopsy needle beyond which an ultrasound image of the biopsy needle experiences substantial deterioration.

19. The simplified user interface of claim 18, wherein said critical angle is about 5 to 8 degrees.

20. A method for generating an ultrasound display of a target region into which a specular reflector is inserted, the ultrasound display resulting from ultrasonic beams generated by an ultrasound probe having an array of transducers thereon, the specular reflector forming a first angle with respect to the transducer array, comprising the steps of:

generating a first frame according to a first set of frame parameters directed to the imaging of the target region;

generating a second frame according to a second set of frame parameters directed to the imaging of the specular reflector;

modifying said first frame with information from said second frame relating to the location and orientation of the specular reflector; and displaying an output image derived from said modified first frame;

wherein said first and second sets of frame parameters are selected such that scan lines associated with said second frame are steered at a steering angle with respect to an axis of the ultrasound probe, said steering angle being closer to the first angle than a corresponding angle associated with scan lines of said first frame;

and wherein lateral focusing depths associated with respective scan lines of said second frame vary on a per-scan-line basis, according to a varying distance along each scan line between the transducer array and the specular reflector.

21. The method of claim 20, wherein said first and second sets of frame parameters are selected such that an elevation beam width of said second frame is greater than an elevation beam width of said first frame.

22. The method of claim 20, wherein said step of modifying said first frame with information from said second frame comprises the step of compounding said first frame with said second frame.

23. The method of claim 22, further comprising the step of digitally enhancing said second frame to highlight the specular reflector prior to said compounding step.

24. The method of claim 23, said specular reflector being inserted into the target region as part of a medical procedure in which the specular reflector is required to approach a lesion in the target region, further comprising the step of digitally enhancing said first frame to highlight the lesion prior to said compounding step.

25. The method of claim 20, wherein said first and second sets of frame parameters are selected such that said second frame comprises fewer scan lines than said first frame.

26. The method of claim 20, wherein said first angle varies depending on a manual positioning of the specular reflector and the ultrasound probe by a user, and wherein said first angle is automatically measured by performing the steps of:

sweeping a series of exploratory ultrasound pulses across a range of angles in said target region; and using echoes corresponding to said exploratory ultrasound pulses to compute a measure of said first angle;

wherein said steering angle is dynamically computed based on said measure of said first angle.

27. The method of claim 20, wherein said specular reflector comprises a biopsy needle.

28. A computer program product, resident on a computer-readable medium, for use in an ultrasound system, the computer program product for use by the ultrasound system in generating an ultrasound display of a target region into which a specular reflector is inserted, comprising:

computer code for generating a first frame according to a first set of frame parameters directed to the imaging of the target region;

computer code for generating a second frame according to a second set of frame parameters directed to the imaging of the specular reflector;

computer code for modifying said first frame with information from said second frame relating to a location and orientation of the specular reflector; and computer code for displaying an output image derived from said modified first frame;

wherein said first and second sets of frame parameters are selected such that an elevation beam width of said second frame is greater than an elevation beam width of said first frame.

29. A computer program product, resident on a computer-readable medium, for use in an ultrasound system having an ultrasound probe with an array of transducers thereon, the computer program product for use by the ultrasound system in generating an ultrasound display of a target region into which a specular reflector is inserted, the specular reflector forming a first angle with respect to the transducer array, comprising:

computer code for generating a first frame according to a first set of frame parameters directed to the imaging of the target region;

computer code for generating a second frame according to a second set of frame parameters directed to the imaging of the specular reflector;

computer code for modifying said first frame with information from said second frame relating to the location and orientation of the specular reflector; and computer code for displaying an output image derived from said modified first frame;

wherein said first and second sets of frame parameters are selected such that scan lines associated with said second frame are steered at a steering angle with respect to an axis of the ultrasound probe, said steering angle being closer to said first angle than a corresponding angle associated with scan lines of said first frame;

and wherein lateral focusing depths associated with respective scan lines of said second frame vary on a per-scan-line basis, according to a varying distance along each scan line between the transducer array and the specular reflector.

* * * * *